United States Patent
Stöber

(10) Patent No.: US 7,376,251 B2
(45) Date of Patent: May 20, 2008

(54) ELECTRONIC IMAGE EVALUATING DEVICE AND EVALUTION METHOD

(75) Inventor: Bernd Rüdiger Stöber, Rheda-Wiedenbrück (DE)

(73) Assignee: Koenig & Bauer Aktiengesellschaft, Wurzburg (DE)

( * ) Notice: Subject to any disclaimer, the term of this patent is extended or adjusted under 35 U.S.C. 154(b) by 810 days.

(21) Appl. No.: 10/504,156

(22) PCT Filed: Feb. 22, 2003

(86) PCT No.: PCT/DE03/00569

§ 371 (c)(1),
(2), (4) Date: Aug. 23, 2004

(87) PCT Pub. No.: WO03/073084

PCT Pub. Date: Sep. 4, 2003

(65) Prior Publication Data

US 2005/0213822 A1    Sep. 29, 2005

(30) Foreign Application Priority Data

Feb. 26, 2002    (DE) ................. 102 08 286

(51) Int. Cl.
*G06K 9/00*    (2006.01)

(52) U.S. Cl. ................ 382/112; 382/201; 250/559.01; 250/559.02; 356/429

(58) Field of Classification Search ............... 382/112, 382/145, 147, 201; 101/2, 84, 93.03, 93.04, 101/212; 250/548, 559.01, 559.02, 559.04, 250/559.07, 559.09, 559.39, 564; 347/19; 358/3.3, 3.31, 3.32; 702/81, 182

See application file for complete search history.

(56) References Cited

U.S. PATENT DOCUMENTS

| 5,056,430 | A |   | 10/1991 | Bayerlein et al. |
| 5,237,181 | A | * | 8/1993 | Kerkhoff et al. ....... 250/559.08 |
| 5,256,883 | A | * | 10/1993 | Weichmann et al. ... 250/559.39 |
| 5,384,859 | A |   | 1/1995 | Bolza-Schunemann |
| 5,471,309 | A | * | 11/1995 | Bolza-Schunemann ..... 356/394 |
| 5,724,259 | A | * | 3/1998 | Seymour et al. ............ 382/199 |
| 2002/0018600 | A1 |   | 2/2002 | Lyon et al. |

FOREIGN PATENT DOCUMENTS

| DE | 1966 795 | 8/1974 |
| DE | 38 09 941 A1 | 3/1988 |
| DE | 38 32 984 A1 | 9/1988 |
| DE | 41 02 122 A1 | 1/1991 |
| DE | 41 36 461 C2 | 11/1991 |
| EP | 0 809 395 A2 | 11/1997 |
| JP | 63-135252 | 6/1988 |
| WO | WO 91/14173 | 9/1991 |
| WO | WO 00/42381 | 7/2000 |

\* cited by examiner

Primary Examiner—Abolfazl Tabatabai
(74) Attorney, Agent, or Firm—Jones, Tullar & Cooper, PC

(57) ABSTRACT

An electronic image evaluating device includes at least one area sensor that is provided with a plurality of photosensitive pixels. Each of these pixels will emit an electric output signal in response to the light input signal that it receives. The intensity of the electric output signal correlates with the light input signal. This electric output signal is evaluated in an evaluation unit as image information. The pixels of the area sensor can be controlled and evaluated individually, or in groups. Any sector of the maximum monitorable scanning area can be selectively evaluated.

29 Claims, 2 Drawing Sheets

ELECTRONIC IMAGE EVALUATING DEVICE AND EVALUTION METHOD

CROSS-REFERENCE TO RELATED APPLICATIONS

This patent application is the U.S. National Phase under 35 USC 371 of PCT/DE 03/00569, filed Feb. 22, 2003; published as WO 03/073084 A1 on Sep. 4, 2003 and claiming priority to DE 102 08 286.3, filed Feb. 26, 2002, the disclosures of which are expressly incorporated herein by reference.

FIELD OF THE INVENTION

The present invention is directed to a method for using an electronic image evaluating device. The device has at least one area sensor with a plurality of light-sensitive pixels. The pixels can be triggerable and evaluated individually or in groups.

BACKGROUND OF THE INVENTION

Electronic image evaluating devices for checking printed products are known, with which evaluating devices defined features of a printed product can be recorded and evaluated. Normally, individually adapted sensors or cameras are used for checking these special features. Since the position of these features, or the number of features to be evaluated can be basically arbitrary, the number and positioning of the appropriate sensors or cameras of the image evaluating device must be adapted correspondingly. Therefore, when using such camera or sensor systems adapted to individual features, it is necessary for the individual sensors or cameras to be adjustably situated so that they can be positionable above various positions of the features to be evaluated.

Measuring or dependable assessment of the features to be evaluated requires a fixed scale of both image dimensions. The fixed scale can only be assured by recording an image by the use of area image sensors, because the image sensor area itself constitutes this spatial interrelation of the imaged objects with respect to each other. In line camera systems, the spatial interrelation of the imaged objects is not assured with the required dependability because of the chronological synchronization of the image lines, which cannot always be maintained.

US 2002/0018600 A1 describes an image scanner, whose sensor field is selectively read out.

DE 41 36 461 C2 discloses a device for inspecting large areas of printed products. This device uses several parallel operated area sensors.

WO 00/42381 A1 describes an image evaluating device with an area sensor having a plurality of light-sensitive pixels. The pixels can be individually evaluated, so that freeely selectable segments can be selectively evaluated.

EP 809 395 A2 discloses a method for operating an area sensor. Each pixel can be selected and can be evaluated individually or in groups.

SUMMARY OF THE INVENTION

The object of the present invention is directed to providing an electronic image evaluating device and to providing a method for evaluation.

In accordance with the invention, the object is attained by providing an electronic image evaluating device having at least one area sensor having a plurality of light-sensitive pixels. Each such pixel emits an electrical output signal as a function of the light input signal it receives. The strength of the electrical output signal can be evaluated in an evaluation unit as image information. The pixels of the area sensor can be triggerable and evaluated individually or in groups. Freely selectable segments of the maximally observable scanning area can be selectively evaluated. The image to be evaluated may be a printed product that is conveyed past the area sensor. The segments selected by the individual area sensors may be selected at a function of the conveying movement. A flash device may be provided for illuminating the image. A reference marker can be applied to the image.

The invention is based on the basic concept of employing area sensors for the electronic image evaluating device, with the area sensors having pixels that can be selected and evaluated individually and/or in groups. Such freely addressable area sensors permit the choosing of freely selectable segments from the maximally observable scanning area of the area sensor, which observable scanning area results from the size of the area sensor and the optical device appropriately arranged in front of it. Only the image data from these selected segments is passed on to a downstream-located electronic evaluation device, so that the selected image data can be evaluated there. The remaining segments of the maximum scanning area are blanked out and are not taken into account in the electronic evaluation device. As a result, it is possible to select the image data to be evaluated, depending on the application, by the use of an appropriate triggering of the area sensor. Thus, the features to be evaluated can be recorded at any arbitrary position on the printed product without a mechanical displacement or an adjustment of the individual sensors being necessary.

Furthermore, the pixels of at least one area sensor, for example a CMOS or complementary metal oxide silicon sensor, can also be read out only partially. Individual image areas can thus be selectively blanked out in order to reduce the amount of image data to be processed. From these data, it is possible to determine the position of a segment, as well as to obtain image data of a segment with reduced resolution.

These CMOS sensors have an image structure corresponding to a memory module, so that individual pixels can be interrogated like memory cells. Thus, only image elements which are actually intended to be evaluated need to be read out.

To be able to increase the scanning area which can maximally be observed by the image evaluating device, without having to employ correspondingly larger and larger area sensors, it is possible to provide several area sensors in the image evaluating device. The image data from the several individual area sensors are evaluated together in the downstream located evaluating device. As a result, it is possible to achieve, by the combination of several area sensors, the evaluation of a very large maximally observable scanning area with the image evaluating device by using relatively inexpensive standard components.

So that, when employing several individual area sensors, no areas are formed which cannot be evaluated, the maximally observable scanning areas of the several individual area sensors should overlap at least slightly. The image data emanating from the overlapping areas can then be taken into consideration in the downstream-located image evaluating device in such a way that any such overlapping area is evaluated only once.

In order to be able to evaluate a printed product with great effectiveness, by utilization of the image evaluating device, a conveying arrangement should be provided in the image evaluating device, by the use of which conveying arrangement the printed product can be conveyed past the area sensor. In this connection, it is particularly advantageous if the pixels of the several individual area sensors can be selected and evaluated as a function of the conveying movement of the printed product. As a result, it can be achieved that the segments selected for observation by the several individual area sensors are selected as a function of the conveying movement of the printed product.

Sufficient illumination of the printed product is often required for dependable image evaluation. An illumination arrangement, in particular a flash illumination arrangement, should therefore be provided in the image evaluating device.

As an alternative to flash illumination, it is also possible to employ a constant light illumination, if an electronic full image shutter is provided.

The full image shutter limits the chronological integration of the light in the image sensor in an electronic way.

Electronic image evaluating devices are often used for electronically evaluating webs of printed material, which webs have been repeatedly imprinted with a recurring pattern. With such evaluation tasks, it is particularly advantageous if a reference marker is assigned to each individual pattern on the web of imprinted material. In this case, a sensor arrangement, by the use of which the reference markers can be detected, should be provided in the electronic image evaluating device. With this sensor arrangement, it is possible for the sensor device to emit a synchronizing signal, by the use of which synchronizing signal the image evaluating device can be synchronized with the movement of the web of imprinted material.

BRIEF DESCRIPTION OF THE DRAWINGS

Preferred embodiments of the present invention are represented in the drawings and will be described in greater detail in what follows.

Shown are in.

DESCRIPTION OF THE PREFERRED EMBODIMENT

Figure 1:
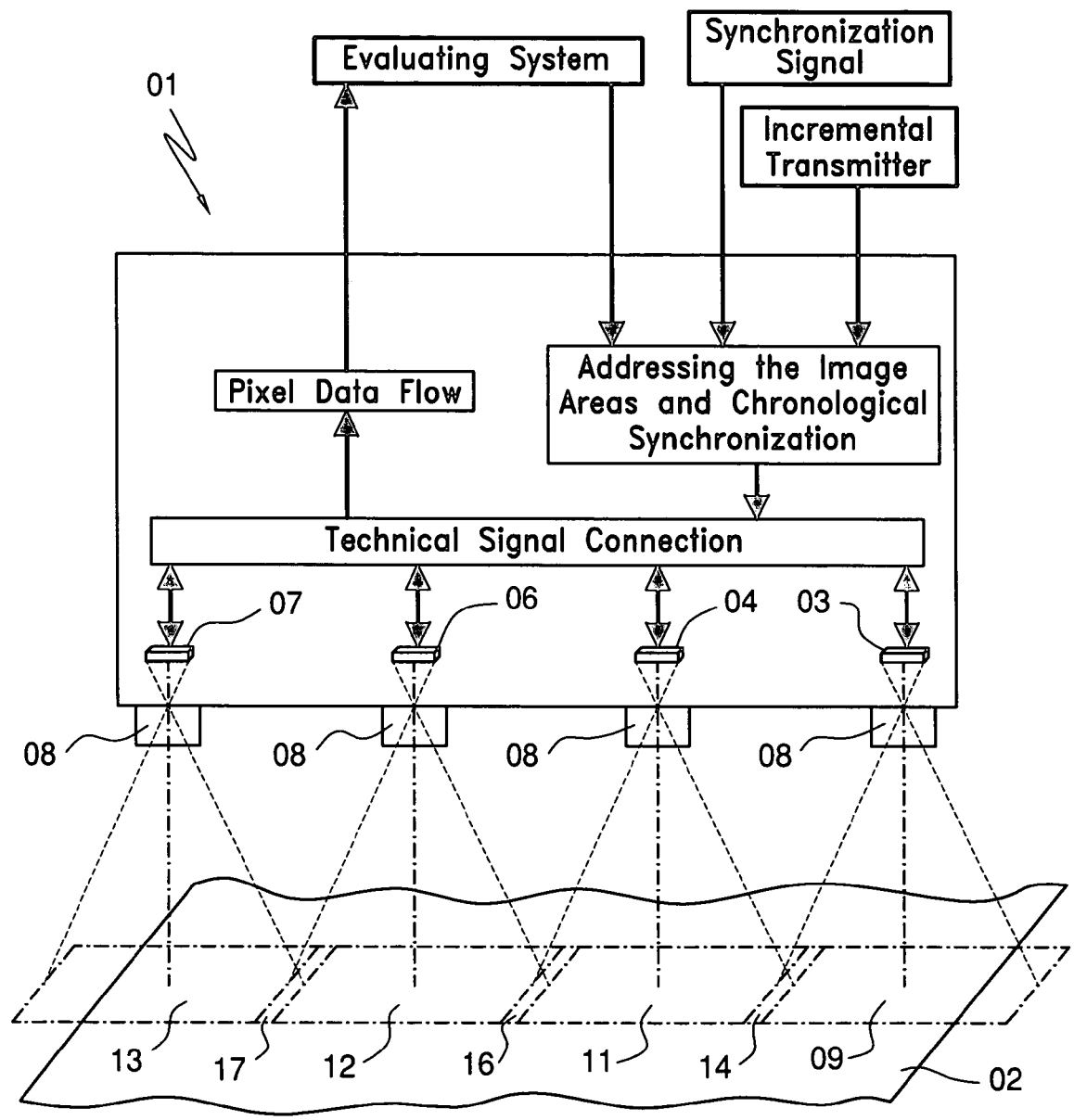
FIG. 1, a schematic depiction of the structure of an image evaluating device in accordance with the present invention, and in FIG. 2, a perspective plan view of a printed product to be evaluated with various features to be evaluated.

Referring initially to FIG. 1, there may be seen an image evaluating device, generally at 01, in accordance with the present invention. In the image evaluating device 01, which is schematically represented in FIG. 1, a web 02 of imprinted material can be conveyed underneath an area sensor system with four individual area sensors 03, 04, 06 and 07. These individual area sensors 03, 04, 06, and 07 are arranged on a common support element. An optical unit 08 is assigned to each of the individual area sensors 03 to 07, by the use of which optical units 08 a defined image area of the web 02 of imprinted material is produced on the light-sensitive pixels of the several individual area sensors 03 to 07.

Maximally observable scanning areas 09, 11, 12 and 13 are a result of the type of area sensors 03 to 07 used, the properties of the optical units 08 used with the area sensors and the distance between the optical units 08 and the web 02 of imprinted material, which web 02 of imprinted material can be evaluated by the use of the area sensors 03 to 07. Each of the maximally observable scanning areas 09 to 13 is approximately rectangular. Adjoining scanning areas 09, 11, 12 and 13 overlap in overlap areas 14, 16 and 17 respectively. As a result, it is possible, by the combination of the area sensors 03 to 07 to evaluate a total scanning area, which is rectangular as a whole, and whose width is slightly greater than a width of the web 02 of imprinted material to be evaluated.

Figure 2:
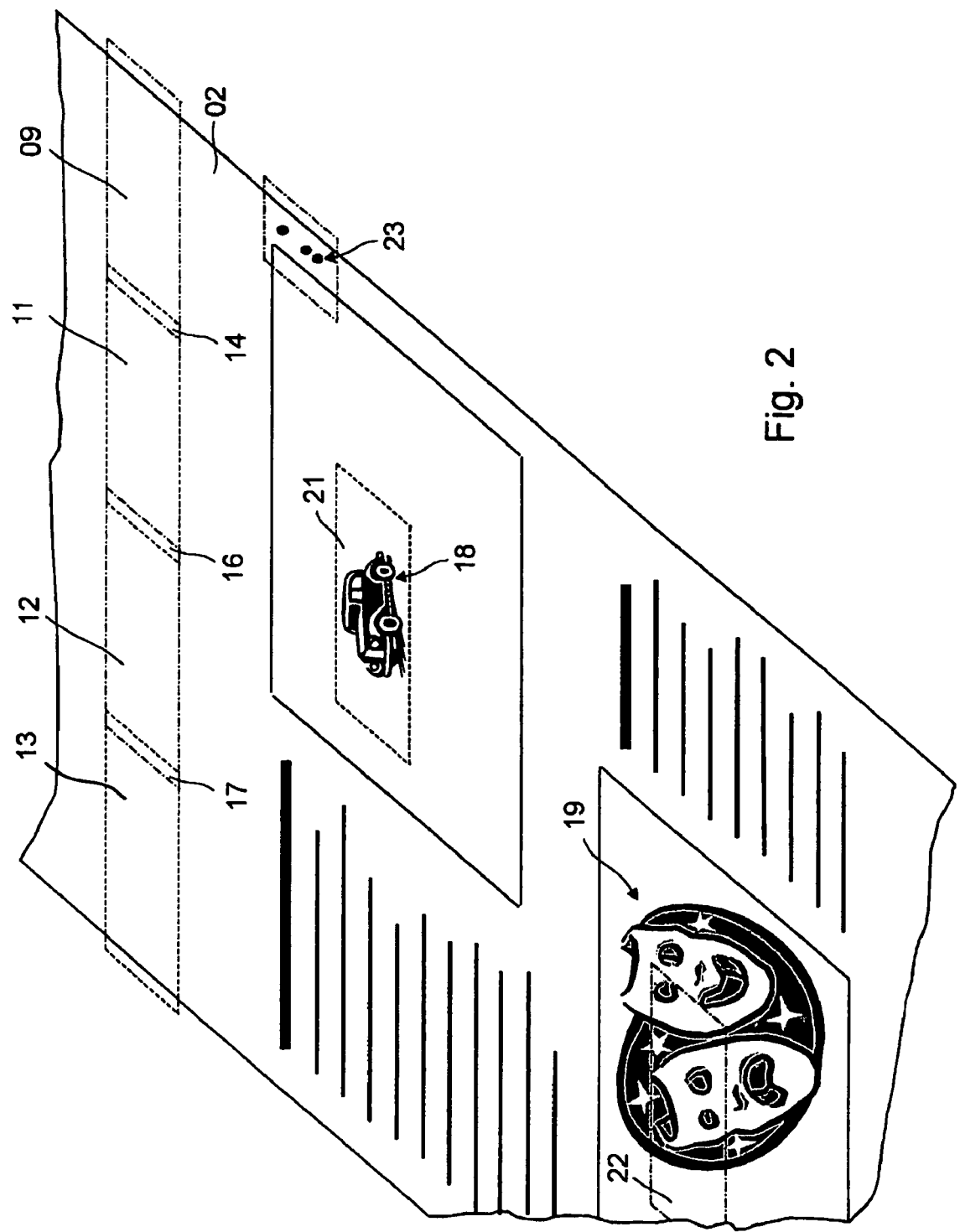

The web 02 of imprinted material to be evaluated is represented in printed form in FIG. 2. Representative image patterns 18 and 19 have been imprinted on the web 02 of imprinted material in repeated patterns. Furthermore, a reference marker 23 which is assigned to each image pattern, has been imprinted on the web 02 of imprinted material. For evaluating the result of printing on the web 02 of imprinted material, it is now intended to selectively evaluate respective rectangular segments 21 and 22 of the printed image in the area of the image patterns 18 and 19, and to compare these evaluated rectangular segments 21 and 22 of the printed image patterns 18 and 19 with reference data.

The reference marker 23 can also represent a detection area which could be judged, for example in regard to the positions of the color fields with respect to each other; i.e. for register measuring. The reference marker 23 can also be used for pattern reference.

The detection of the reference marker 23 does not necessarily have to be performed with the multi-area sensor system itself. An additional sensor can also be provided, which is only logically assigned to the system. Moreover, synchronization with the pattern could also be derived from a machine signal.

The web 02 of imprinted material to be evaluated is conveyed underneath the several individual area sensors 03 to 07. As soon as the reference marker 23 has been detected, an appropriate synchronization signal is generated, so that thereafter first the image pattern segment 21, and subsequently the image pattern segment 22 can be recorded, positionally correct, by use of the several individual image sensors 03 to 07 and these segments 21 and 22 can be evaluated. In the course of this evaluation, only the pixels of the individual area sensors 03 and 07 are triggered, so that only the segments 21 and 22 are recorded. The remaining areas of the web 02 of imprinted material which are passed underneath the image sensors 03 to 07 are blanked out and are not recorded or evaluated.

While a preferred embodiment of a method for using an electronic image evaluating device, in accordance with the present invention, has been set forth fully and completely hereinabove, it will be apparent to one of skill in the art that various changes in, for example the structure of the web conveying assembly, the number of individual area sensors utilized and the like could be made without departing from the true spirit and scope of the present invention which is accordingly to be limited only by the following claims.

What is claimed is:

1. A method for evaluating an image including:
providing an electronic image evaluating device;
providing at least one area sensor, having a maximally observable scanning area, in said electronic image evaluating device;
providing a plurality of light-sensitive pixels in said at least one area sensor, each of said pixels emitting an electrical output signal as a function of a light input signal received by each said pixel;
correlating a strength of each said electrical output signal with said light input signal received by each said pixel;
providing an evaluation unit;
using said evaluation unit for evaluating said electrical output signals as image information;

triggering said pixels in each said at least one area sensor selecting individually and as a group;
evaluating freely selectable signals of said maximally observable scanning area;
providing said image as a printed product;
providing said printed product as a web of imprinted material imprinted with a repeating pattern; assigning a reference marker to each said pattern;
providing a conveying arrangement in said electronic image evaluating device;
using said conveying arrangement for conveying said web having said printed product past said at least one area sensor; and
selecting said signals of said maximally observable scanning area of said at least one area sensor as a function of a conveying movement of said web having said printed product.

2. The method of claim 1 further including providing a plurality of said area sensors in said electronic image evaluating device.

3. The method of claim 2 further including providing said maximally observable scanning area of each said area sensor as a rectangle.

4. The method of claim 2 further including providing said plurality of said area sensors having overlap areas of said maximally observable scanning areas.

5. The method of claim 2 further providing providing said maximally observable scanning areas of said plurality of area sensors as a rectangular total scanning area.

6. The method of claim 2 further including providing a support element and arranging said plurality of said area sensors on said support element.

7. The method of claim 1 further including providing an illumination device for said electronic image evaluating device.

8. The method of claim 7 further including providing said illumination device as a flash device generating flashes at a defined repeat frequency.

9. The method of claim 7 further including providing said illumination device as a full image shutter.

10. The method of claim 1 further including providing said maximally observable scanning area as a rectangle.

11. The method of claim 1 further including providing an illumination arrangement in said electronic image evaluating device.

12. The method of claim 11 further including providing said illumination arrangement as a flash illumination device.

13. The method of claim 12 further including providing said flash illumination device being capable of generating flashes at a defined repeating frequency.

14. The method of claim 1 further including providing a full image shutter in said electronic image evaluating device.

15. The method of claim 1 further including providing a sensor for synchronizing said electronic image evaluating device with movement of said web.

16. The method of claim 15 further including providing said sensor in said electronic image evaluating device.

17. The method of claim 15 including providing said sensor separate from said electronic image device.

18. The method of claim 1 further including providing an optical device for said at least one area sensor.

19. The method of claim 1 further including providing said at least one area sensor as a CMOS sensor.

20. A method for evaluating an image including:
providing an electronic image evaluating device;
providing at least one area sensor, having a maximally observable scanning area, in said electronic image evaluating device;
providing a plurality of light-sensitive pixels in said at least one area sensor, each of said pixels emitting an electrical output signal as a function of a light input signal received by each said pixel;
correlating a strength of each said electrical output signal with said light input signal received by each said pixel;
providing an evaluation unit;
using said evaluation unit for evaluating said electrical output signals as image information;
triggering said pixels in each said at least one area sensor selecting individually and as a group;
evaluating freely selectable signals of said maximally observable scanning area;
providing said image as a printed product;
providing said printed product as a web of imprinted material imprinted with a repeating pattern;
assigning a reference marker to each said pattern;
providing means for moving said web of material past said electronic image evaluating device; and
synchronizing said web movement past said electronic image evaluating device using said reference marker.

21. The method of claim 20 further including providing an illumination arrangement in said electronic image evaluating device.

22. The method of claim 21 further including providing said illumination arrangement as a flash illumination device.

23. The method of claim 22 further including providing said flash illumination device being capable of generating flashes at a defined repeating frequency.

24. The method of claim 20 further including providing a full image shutter in said electronic image evaluating device.

25. The method of claim 20 further including providing a sensor for synchronizing said electronic image evaluating device with movement of said web.

26. The method of claim 25 further including providing said sensor in said electronic image evaluating device.

27. The method of claim 25 including providing said sensor separate from said electronic image device.

28. The method of claim 20 further including providing an optical device for said at least one area sensor.

29. The method of claim 20 further including providing said at least one area sensor as a CMOS sensor.

* * * * *

UNITED STATES PATENT AND TRADEMARK OFFICE
CERTIFICATE OF CORRECTION

PATENT NO. : 7,376,251 B2 Page 1 of 1
APPLICATION NO. : 10/504156
DATED : May 20, 2008
INVENTOR(S) : Bernd Rudiger Stober It is certified that error appears in the above-identified patent and that said Letters Patent is hereby corrected as shown below:

In Col. 5, line 7
clause starting with "assigning a" should begin on next line

In Col. 5, line 27
replace "providing providing"
with --providing.--

Signed and Sealed this

Twenty-second Day of July, 2008

JON W. DUDAS
*Director of the United States Patent and Trademark Office*